US011718882B2

(12) United States Patent
Jeon

(10) Patent No.: US 11,718,882 B2
(45) Date of Patent: Aug. 8, 2023

(54) EML4-ALK GENE MUTATION ANALYSIS METHOD

(71) Applicant: CYTOGEN, INC., Seoul (KR)

(72) Inventor: Byung Hee Jeon, Seongnam-si (KR)

(73) Assignee: CYTOGEN, INC., Seoul (KR)

( * ) Notice: Subject to any disclaimer, the term of this patent is extended or adjusted under 35 U.S.C. 154(b) by 124 days.

(21) Appl. No.: 16/631,324

(22) PCT Filed: Jul. 17, 2018

(86) PCT No.: PCT/KR2018/008046
§ 371 (c)(1),
(2) Date: Jan. 15, 2020

(87) PCT Pub. No.: WO2019/031722
PCT Pub. Date: Feb. 14, 2019

(65) Prior Publication Data
US 2020/0140959 A1 May 7, 2020

(30) Foreign Application Priority Data
Aug. 7, 2017 (KR) .................. 10-2017-0099591

(51) Int. Cl.
*C12Q 1/6886* (2018.01)
*C12Q 1/6806* (2018.01)
*C12Q 1/6827* (2018.01)

(52) U.S. Cl.
CPC ......... *C12Q 1/6886* (2013.01); *C12Q 1/6806* (2013.01); *C12Q 1/6827* (2013.01); *C12Q 2549/119* (2013.01); *C12Q 2600/106* (2013.01); *C12Q 2600/158* (2013.01); *G01N 2800/7028* (2013.01)

(58) Field of Classification Search
CPC .................. C12Q 2549/119; G01N 2800/7028
See application file for complete search history.

(56) References Cited

U.S. PATENT DOCUMENTS

| | | | |
|---|---|---|---|
| 2013/0330719 A1 | 12/2013 | Sanders et al. | |
| 2020/0249232 A1* | 8/2020 | Konstantopoulos | G01N 33/5091 |

FOREIGN PATENT DOCUMENTS

| | | | |
|---|---|---|---|
| CN | 101466721 A | 6/2009 | |
| CN | 102719525 A | 10/2012 | |
| CN | 103397045 A | 11/2013 | |
| CN | 104685356 A | 6/2015 | |
| CN | 104818320 A | 8/2015 | |
| CN | 106148525 A | 11/2016 | |
| JP | 2012-100628 A | 5/2012 | |
| KR | 10-2011-0115478 A | 10/2011 | |
| KR | 10-1226515 B1 | 1/2013 | |
| KR | 10-1254679 B1 | 4/2013 | |
| KR | 10-1254680 B1 | 4/2013 | |
| KR | 10-2016-0001304 A | 1/2016 | |
| KR | 20160001304 | * 1/2016 | ............... C12Q 1/68 |
| WO | 2010/132888 A2 | 11/2010 | |
| WO | 2011/130635 A2 | 10/2011 | |
| WO | WO-2011130635 A2 | * 10/2011 | ........... C12Q 1/6886 |
| WO | 2017/181183 A1 | 10/2017 | |

OTHER PUBLICATIONS

Riahi, R. et al., A novel microchannel-based device to capture and analyze circulating tumor cells (CTCs) of breast cancer, Int. J. Oncol., vol. 44, pp. 1870-1878 (Year: 2014).*
Buck, G.A. et al., Design Strategies and Performance of Custom DNA Sequencing PrimersBiotechniques, vol. 27, pp. 528-536 (Year: 1999).*
Loutherback, K. et al. Deterministic seaparation of cancer cells from blood at 10 mL/min, AIP Advances, vol. 2, Apr. 21, 2007, pp. 1-7 (Year: 2012).*
Yusa et al., Development of a New Rapid Isolation Device for Circulating Tumor Cells (CTCs) Using 3D Palladium Filter and Its Application for Genetic Analysis, PLOS One, vol. 9, e88821, pp. 1-11 (Year: 2014).*
Sam H. Au et al., "Microfluidic Isolation of Circulating Tumor Cell Clusters by Size and Asymmetry", Scientific Reports, May 26, 2017, pp. 1-10, vol. 7: 2433.
International Search Report of PCT/KR2018/008046 dated Feb. 15, 2019 [PCT/ISA/210].
Kim et al., "Enrichment of cancer cells from whole blood using a microfabricated porous filter", Analytical Biochemistry, vol. 440 (2013) pp. 114-116 (4 pages total).
Oh et al., "A New Size-based Platform for Circulating Tumor Cell Detection in Colorectal Cancer Patients", Clinical Colorectal Cancer, vol. 16, No. 3, 2017, pp. 214-219 (6 pages total).
Lee et al., "Evaluation of a novel approach to circulating tumor cell isolation for cancer gene panel analysis in patients with breast cancer", Oncology Letters, vol. 13, pp. 3025-3031, 2017 (8 pages total).
Jeon et al., "Abstract 1737: ALK rearrangement analysis in circulating tumor cells of lung cancer patients", Cancer Research, Proceedings of the American Association for Cancer Research Annual Meeting 2017, Washington, DC, Apr. 1-5, 2017 (4 pages total).
Notice of Reasons for Refusal dated Mar. 2, 2021 from the Japanese Patent Office in JP Application No. 2020-504378.
Extended European Search Report dated Apr. 9, 2021 from the European Patent Office in EP Application No. 18843071.4.

(Continued)

*Primary Examiner* — Teresa E Strzelecka
(74) *Attorney, Agent, or Firm* — Sughrue Mion, PLLC

(57) ABSTRACT qRT-PCR primers capable of detecting EML4-ALK gene variant based on circulating tumor cells at a more sensitive detection limit than a conventional method. Also disclosed is a lung cancer patient screening method which is capable of detecting EML4-ALK gene variant using circulating tumor cells even in a lung cancer patient on whom ALK-FISH testing has been difficult to perform, due to difficulty in collecting a solid lung cancer tissue sample, and is able to determine whether an anticancer drug targeting the EML4-ALK gene variant may be applied to the lung cancer patient.

13 Claims, 13 Drawing Sheets

Specification includes a Sequence Listing.

(56) References Cited

OTHER PUBLICATIONS

Office Action dated May 17, 2022 issued by the Japanese Patent Office in Japanese Application No. 2020-504378.
Chye Ling Tan et al., "Concordance of anaplastic lymphoma kinase (ALK) gene rearrangements between circulating tumor cells and tumor in non-small cell lung cancer", Oncotarget, 2016, vol. 7, No. 17, pp. 23251-23262 (12 pages total).
Eun Hye Kim et al., "Enrichment of cancer cells from whole blood using a microfabricated porous filter", Analytical Biochemistry, 2013, vol. 440, No. 1, pp. 1-3 (3 pages total).
P. Du et al., "Current status of molecular targeted drugs for EML4-ALK-positive non-small cell lung cancer", Chinese Journal of New Drugs, Aug. 2015, vol. 24, No. 16 (1 page total).
Office Action dated Feb. 25, 2023 in Chinese Application No. 201880048104.6.

\* cited by examiner

EML4-ALK GENE MUTATION ANALYSIS METHOD

CROSS REFERENCE TO RELATED APPLICATIONS

This application is a National Stage of International Application No. PCT/KR2018/008046, filed Jul. 17, 2018, claiming priority to Korean Patent Application No. 10-2017-0099591, filed Aug. 7, 2017, the entire disclosures of which are incorporated herein by reference.

TECHNICAL FIELD

The present invention relates to a method for detecting EML4-ALK variants, and more particularly to a PCR primer pair for detecting EML4-ALK variant based on circulating tumor cells, a method of detecting EML4-ALK variant using nested PCR, and a method of screening a non-small cell lung cancer patient for an anticancer drug using blood-derived cancer cells from the non-small cell lung cancer patient.

BACKGROUND ART

Lung cancer is common cancer among Koreans, ranking fourth (10.3%) among cancer cases (202,053 patients) diagnosed in 2010 in South Korea. However, lung cancer has a 5-year survival rate of 19.7% and a worse prognosis than other cancers. Lung cancer is classified into non-small cell lung cancer and small cell lung cancer, based on the size and shape of cancer when viewed under a microscope, and non-small cell lung cancer and small cell lung cancer classified in this manner have different clinical courses and treatments. According to the Korea Central Cancer Registry data published in 2011, 192, 561 cancer cases occurred in 2009 in Korea, and among them, 14,300 non-small cell lung cancer cases occurred among men and women and accounted for 72.6% of total lung cancer cases (19,685 cases). The sex ratio of men and women was 2.5:1, indicating that non-small cell lung cancer occurred more in men than in women (data published by the Korea Central Cancer Registry of the Ministry of Health and Welfare on Dec. 29, 2011). ALK-positive non-small cell lung cancer is a lung cancer caused by the fusion of two genes, ALK and EML4, and it was reported that non-small cell lung cancer patients with EML4-ALK gene variants account for 4 to 7% (7% for Oriental) of total lung cancer patients and that ten of 167 Korean non-small cell lung cancer patients have EML4-ALK variants (J. Korean Med. Sci., 27:228-230, 2012).

A targeted anticancer drug for non-small cell lung cancer caused by the EML4-ALK variants is XALKORI (crizotinib) developed by Pfizer. Since Abbott's companion diagnostic test with XALKORI was approved by the US Food and Drug Administration (FDA) in August 2011, it has been widely used in the US Oncologic Community and has become a clinically validated and standardized genetic testing method. In Europe, it was approved as a CE-IVD test, has been used in the medical field since September 2011, and has been mainly used to support academic research and the evaluation of new treatments.

Since the appearance of XALKORI, the paradigm of treatment of non-small cell lung cancer has been shifted from a standard treatment method, which comprises testing EGFR variants and then administering Iressa or a conventional cytotoxic anticancer agent (having a low therapeutic effect and high side effects) depending on the presence or absence of the variant, to a method which comprises testing EGFR and EML4-ALK variants and then selecting a therapeutic method from among Iressa, Xalkori and a conventional cytotoxic anticancer agent. ALK gene variants show various types of gene fusions, and immunohistochemistry, RT-PCR, FISH, etc. may be used as clinical methods for detecting them. Currently, Abbott's Vysis ALK FISH method, approved by the FDA, is used as the standard companion diagnostic test for crizotinib administration, but this method has problems in that it is difficult and complex, requiring a high cost and time to test many patients. In addition, this method has a problem of anatomical features (Lung Cancer 84:39-44, 2014, Cancer Cytopathol. Epub ahead of print 2014.4.10), and thus there is an urgent need for alternatives for this method.

Meanwhile, circulating tumor cells (CTCs) are a small number of tumor cells, which are shed from primary tumor tissue and circulate in blood flow, there are one to thousands of circulating tumor cells per mL of blood depending on the type of cancer.

A test method using circulating tumor cells is a powerful technology capable of replacing conventional biopsy, and has advantages in that it is inexpensive, reduces the patient's pain and the risk of biopsy, and can prolong the patient's life through rapid selection of a targeted drug.

Accordingly, the present inventors have made extensive efforts to develop a genetic testing method enabling the administration of anticancer drugs, for example, crizotinib, even to patients whose lung cancer tissues are difficult to collect, and as a result, have developed a method comprising capturing lung cancer cells present in the form of circulating tumor cells and detecting EML4-ALK variant in the circulating lung cancer cells with high accuracy, thereby completing the present invention.

DISCLOSURE

Technical Problem

An object of the present invention is to provide an EML4-ALK variant-detecting PCR primer pair for detecting EML4-ALK gene variants with high accuracy on the basis of circulating tumor cells. Another object of the present invention is to provide a method for detecting EML4-ALK V1-type variant with high accuracy. Still another object of the present invention is to provide a method for detecting EML4-ALK V3-type variant with high accuracy.

Yet another object of the present invention is to provide a method of screening a non-small cell lung cancer patient through the effectiveness of an anticancer drug for the cancer patient by using blood-derived cancer cells from the cancer patient.

The technical objects to be achieved by the present invention are not limited to the above-mentioned objects, and other technical problems which are not mentioned will be clearly understood by those skilled in the art from the following description.

Technical Solution

To the above objects, a method for analyzing EML4-ALK gene variant according to one aspect of the present invention may comprise the steps of:
obtaining a liquid biopsy sample from a cancer patient;
isolating circulating tumor cells from the liquid biopsy sample using a biochip;
isolating RNA from the isolated circulating tumor cells;

performing qRT-PCR using the isolated RNA as a template and two qRT-PCR primers;

performing nested PCR using a resulting product from the qRT-PCR as a template and two nested primers for the two qRT-PCR primers; and detecting EML-ALK gene variant type based on the resulting product from the nested PCR.

In an embodiment of the present invention, the liquid biopsy sample may be blood.

In an embodiment of the present invention, the cancer may be lung cancer.

In an embodiment of the present invention, the cancer may be non-small cell lung cancer.

In an embodiment of the present invention, the step of isolating the circulating tumor cells may be performed under atmospheric pressure of 1000 hPa to 1020 hPa.

In an embodiment of the present invention, the biochip may be a high-density microporous chip coated with a BSA solution.

In an embodiment of the present invention, the high-density microporous chip may have a size-based chip.

In an embodiment of the present invention, the coating with a BSA solution may be performed at a BSA concentration of 0.05 to 0.15%.

In an embodiment of the present invention, the EML4-ALK gene variant type may be V1 or V3 type.

In an embodiment of the present invention, one of the two qRT-PCR primers may be a forward qRT-PCR primer and the other may be a reverse qRT-PCR primer.

In an embodiment of the present invention, the forward qRT-PCR primer may be one selected from the group consisting of SEQ ID NO: 1, SEQ ID NO: 3 and SEQ ID NO: 4.

In an embodiment of the present invention, the reverse qRT-PCR primer may be SEQ ID NO: 2.

In an embodiment of the present invention, one of the two nested primers may be a forward nested primer and the other may be a reverse nested primer.

In an embodiment of the present invention, the forward nested primer may be one selected from the group consisting of SEQ ID NO: 1, SEQ ID NO: 3, SEQ ID NO: 4 and SEQ ID NO: 10.

In an embodiment of the present invention, the reverse nested primer may be SEQ ID NO: 2 or SEQ ID NO: 9.

To achieve the above technical objects, a method for screening a cancer patient according to another aspect of the present invention may indicate that if the cancer patient's gene variant obtained through the method for analyzing EML4-ALK gene variant according to the present invention corresponds to one selected from the group consisting of (i) exons 1 to 13 of the EML4 gene+exons 20 to 29 of the ALK gene;

(ii) exons 1 to 20 of the EML4 gene+exons 20 to 29 of the ALK gene;

(iii) exons 1 to 6a of the EML4 gene+exons 20 to 29 of the ALK gene;

(iv) exons 1 to 6b of the EML4 gene+exons 20 to 29 of the ALK gene;

(v) exon 15 of the EML4 gene+exons 20 to 29 of the ALK gene;

(vi) exon 14 of the EML4 gene+a linker composed of a 11-bp oligonucleotide+exons 20 to 29 of the ALK gene;

(vii) exon 2 of the EML4 gene+exons 20 to 29 of the ALK gene; and (viii) exon 2 of the EML4 gene+intron 19 of the ALK gene+exons 20 to 29 of the ALK gene, an anticancer drug is effective for the cancer patient.

In an embodiment of the present invention, the cancer may be lung cancer.

In an embodiment of the present invention, the cancer may be non-small cell lung cancer.

In an embodiment of the present invention, the anticancer drug may be crizotinib.

Advantageous Effects

According to embodiments of the present invention, even in lung cancer patients whose lung cancer tissues were difficult to collect, making it impossible to perform ALK-FISH testing, EML4-ALK variants may be detected using circulating tumor cells, whether administration of an anti-cancer drug targeting the EML4-ALK variants is appropriate may be easily determined.

It is to be understood that the effects of the present invention are not limited to the above-described effects and include all effects that can be deduced from the configuration of the present invention described in the detailed description of the invention or the claims.

BEST MODE

Figure 1:
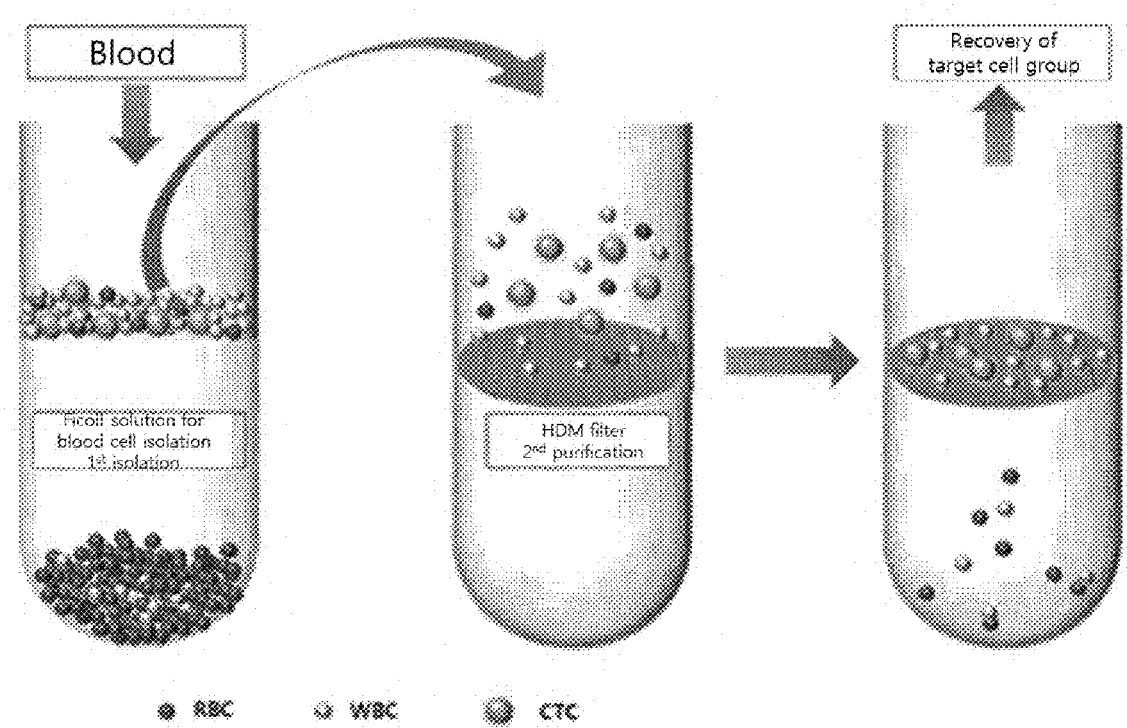
FIG. 1 shows a process of isolating circulating tumor cells.
Figure 2:
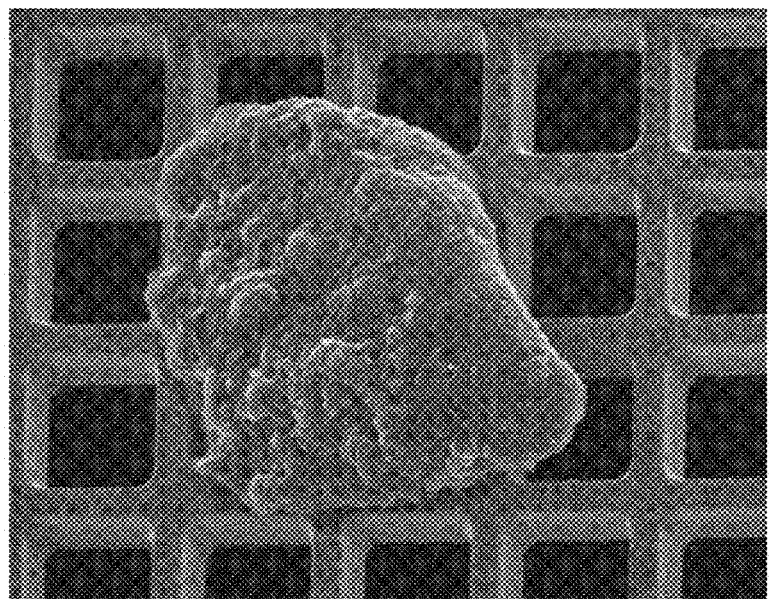
FIG. 2 is a photograph showing circulating tumor cells isolated by a high-density microporous chip.

Hereinafter, examples of the present invention will be described in detail so that those skilled in the technical field to which the present invention pertains art can easily carry out the present invention. However, the present invention may be embodied in various different forms and is not limited to the examples described herein.

Example 1: Fabrication of High-Density Microporous Chip

A high-density microporous chip used in an experiment had a pore size of 5.5 to 8.5 μm and configured such that white blood cells (WBCs) and red blood cells (RBCs) having a size smaller than 5.5 μm would be removed by passage through the chip while target cells having a size larger than 5.5 μm would remain on the chip. Thus, it was a microporous chip designed such that it could selectively recover cells having a specific size.

For reference, an experiment was performed to examine the cell recovery rate of the high-density microporous chip. In the experiment, 10, 100 and 1000 cancer cells from cancer patients were spiked and passed through the chip, and the number of the cells on the chip (cell recovery rate) was examined. The results are shown in Table 1 below.

TABLE 1

| Samples | Number of cells spiked | Number of cells recovered | Cell recovery (%) |
|---|---|---|---|
| 1 | 10 | 9 | 90 |
| 2 | 100 | 86 | 86 |
| 3 | 1000 | 850 | 85 |

The results of calculating the cell recovery rate of the chip showed that the cell recovery rate was about 80% or higher. In order to confirm again that the recovered cells would be cancer cells, the cells were stained with CK antibody which has been used in a cancer assay. As a result, it was confirmed that the cells were all CK-positive, indicating that the cells were cancer cells.

Example 2: Process of Isolating Circulating Tumor Cells (CTCs)

1. Add 250 μl of an antibody polymer to 5 ml of blood, and then mix for about 3 seconds, followed by reaction at room temperature for 20 minutes.
2. Add 5 ml of PBS containing 1% FBS.
3. Carefully place 10 ml of the reaction solution in a 50 ml tube containing 15 ml of Ficoll solution.
4. Centrifuge the solution at 1200 g for 20 minutes to primarily remove blood cells.
5. To prevent the adsorption of unnecessary cells, coat a high-density microporous chip filter with 0.1% BSA solution for 10 minutes, followed by rinsing with PBS.
6. Place the supernatant of the Ficoll on the filter and filter out a trace amount of existing red blood cells by gravity to secondarily isolate highly pure circulating tumor cells. This does not perform centrifugation or treatment such as immunobead treatment, thereby preventing the circulating tumor cells from being damaged.
7. Identify the isolated circulating tumor cells by staining.

Example 3: Short-Term Culture of Isolated Circulating Tumor Cells

The circulating tumor cells isolated by the high-density microporous chip according to the present invention were seeded onto an ultra-low attachment culture plate coated with a neutrally charged hydrophilic hydrogel. The culture plate contained a medium containing 11 ng/ml of insulin, 22 ng/ml of transferrin, 2 ng/ml of EGF and 8 μM of an ROCK inhibitor, and short-term culture of the cells was performed in a cell culture incubator at 37° C. under 5 to 10% $CO_2$ for 14 days from the start of the culture.

Example 4: Confirmation of Circulating Tumor Cells

In order to confirm, by a staining method, that the circulating tumor cells subjected to short term culture according to Example 3 are cancer cells, a cell staining process was performed using the following method.

1. Fix the recovered cells to a slide for staining by performing a cytospin process which is a cell centrifugation technique.
2. Perform a permeabilization process to enable antibody to enter the cells.
3. Perform a washing process with PBS.
4. Make 1% BSA (bovine serum albumin) using PBS and perform a blocking process to reduce non-specific binding and endogenous peroxidase activity.
5. Perform reaction with EpCAM (epithelial cell adhesion molecule), CK (cytokeratin) and CD (cluster of differentiation) 45 as primary antibodies at room temperature for 60 minutes.
6. Perform reaction with fluorescence-labeled secondary antibodies, which bind to the primary antibodies, at room temperature for 60 minutes.
7. Perform a washing process with PBS.
8. To finally stain the cell nucleus, add DAPI (4',6-diamidino-2-phenylindole) solution and cover the sample with a cover glass, followed by reaction at room temperature for 10 minutes.
9. Calculate the proportion of the stained cells and the cell recovery rate according to a manual while observing the stained cells.

Comparative Example 1: Medium-Dependent Change in Cell Count of Cultured Circulating Tumor Cells The division and growth of circulating tumor cells in a cell culture medium, which is generally used in cell culture, and in the culture medium according to the present invention, were comparatively tested. The culture medium that is generally used in cell culture contained 25 nM sodium selenite, 50 nM hydrocortisone, 0.01 mM ethanolamine, 0.01 mM phosphorylethanolamine, 100 pM triiodothyronine, 0.5% (w/v) bovine serum albumin, 10 mM HEPES, 0.5 mM sodium pyruvate, 4.5 mM L-glutamine and 1× antibiotic-antimycotic, and the culture medium according to the present invention was the same as that in Example 3. In addition, culture conditions were the same as those in Example 3, except that a normal culture plate was used.

Figure 3A:
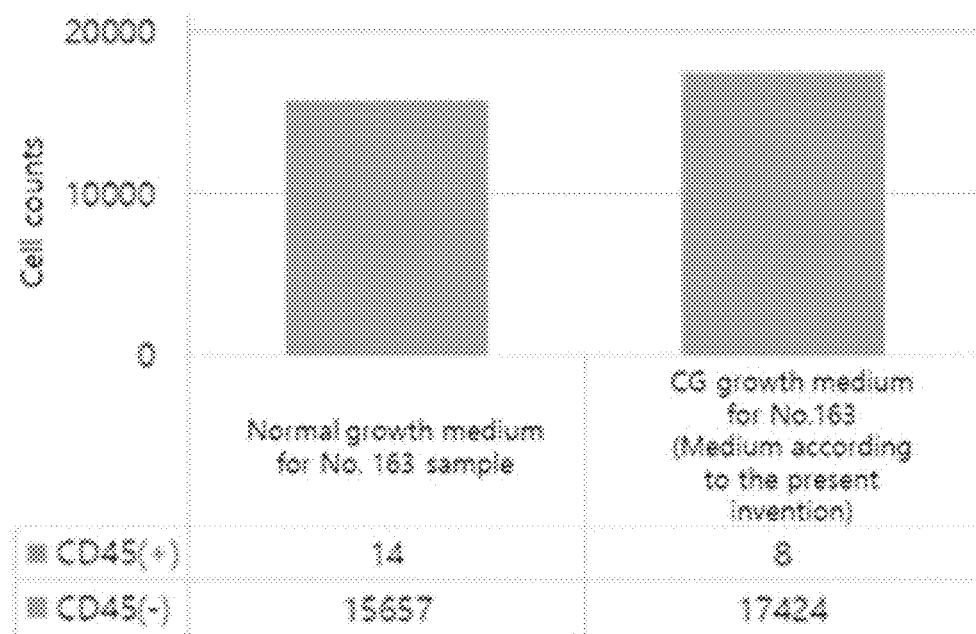
FIGS. 3A and 3B depict graphs showing the growth and division of circulating tumor cells cultured in a medium according to the present invention and the growth and division of circulating tumor cells cultured in a normal culture medium.
Figure 3B:
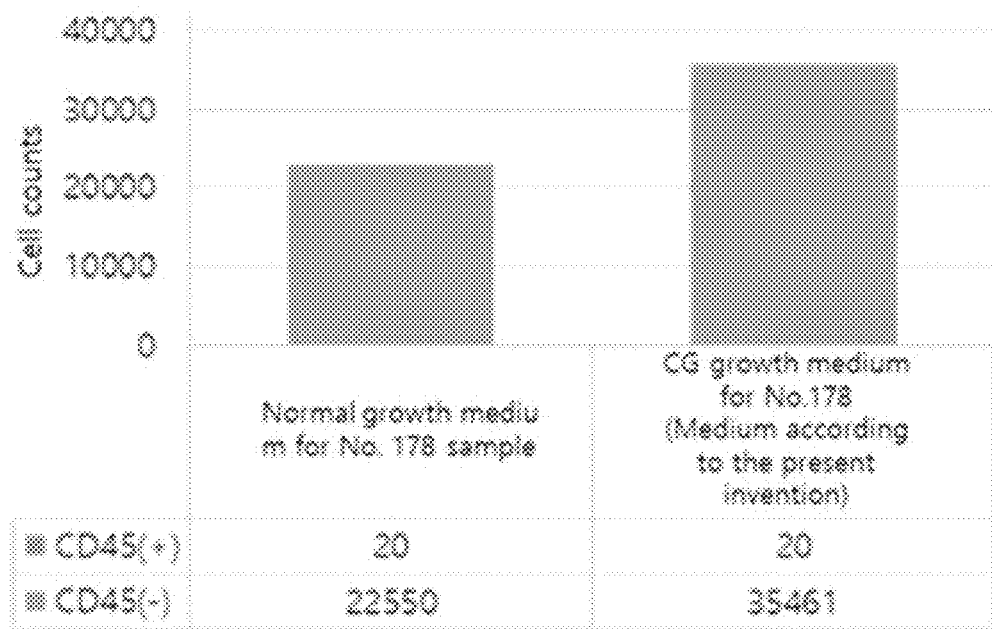

Referring to FIGS. 3A and 3B, CD45—is a biomarker for cultured circulating tumor cells, normal growth medium means a normal cell culture medium, and CG growth medium means the culture medium according to the present invention. FIGS. 3A and 3B show that the cell count of the circulating tumor cells cultured in the culture medium according to the present invention was higher. This suggests that the culture medium according to the present invention is more effective in the division and culture of circulating tumor cells than the normal culture medium.

Comparative Example 2: Medium-Dependent Change in Cell Count of Cultured Circulating Tumor Cells in Hydrogel-Coated Culture Plate In order to measure the effect of the hydrogel-coated culture plate on the growth and division of circulating tumor cells in the presence of the culture medium according to the present invention, comparative culture using a normal culture plate was performed. The culture medium according to the present invention was the same as that in Example 3.

Figure 4A:
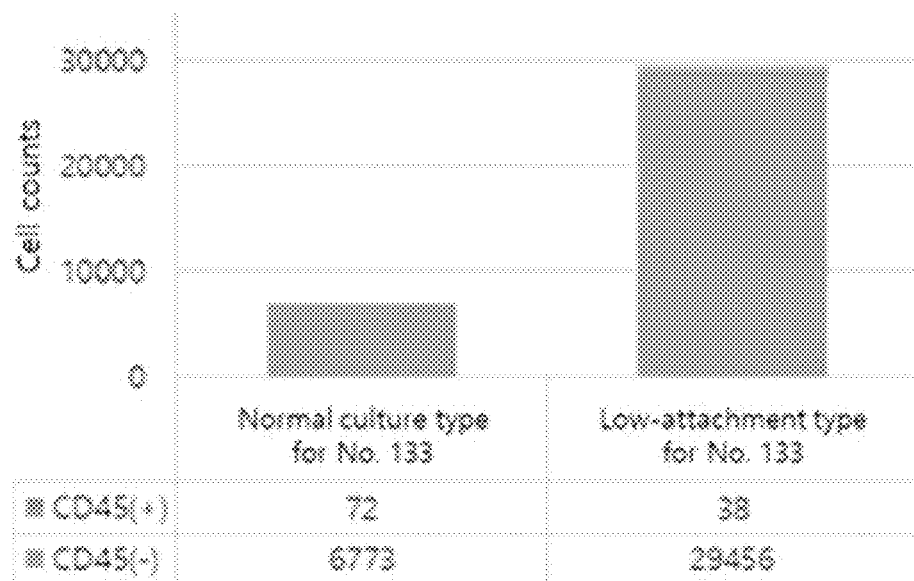
FIGS. 4A and 4B depict graphs showing the growth and division of circulating tumor cells cultured using a medium according to the present invention on a hydrogel-coated culture plate used in the present invention and the growth and division of circulating tumor cells cultured on a normal culture plate.
Figure 4B:
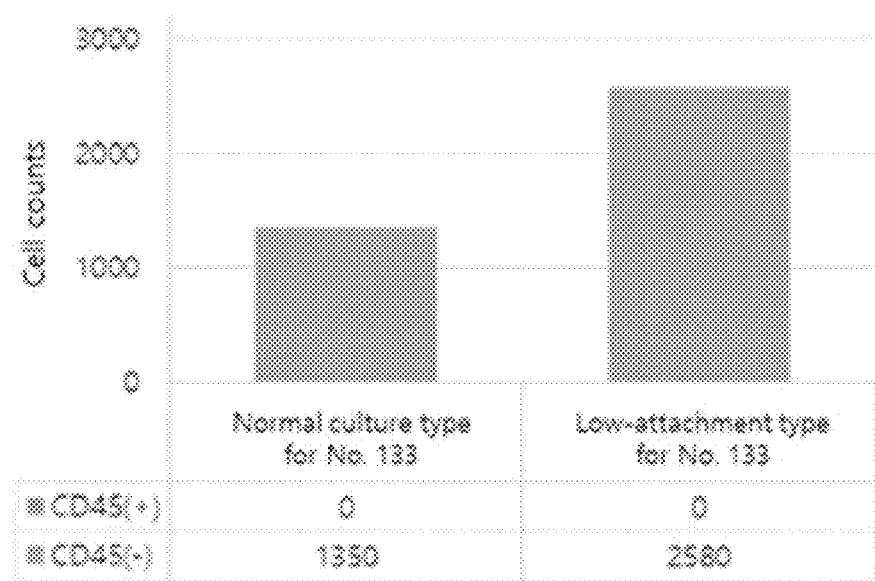

Referring to FIGS. 4A and 4B, normal culture type denotes a normal cell culture plate (cells adhere to the surface of the culture plate), and low attachment type is the hydrogel-coated culture plate used in the present invention. FIGS. 4A and 4B show that the cell count of the circulating tumor cells cultured in the hydrogel-coated culture plate using the culture medium according to the present invention was higher. This suggests that culture in the hydrogel-coated culture plate is more effective in the division and culture of circulating tumor cells.

Example 5: Method of Detecting EML4-ALK V1 Type by qRT-PCR

The H3122 cell line (Matthew Meyerson Department of Medical Oncology, Dana-Farber Cancer Institute, Boston, Mass. 02115), a lung cancer cell line with EML4-ALK V1-type variant, was cultured, and then RNA was extracted therefrom. cDNA was synthesized from the extracted RNA, and the synthesized cDNA was diluted serially and used as a template in qRT-PCR for detecting EML4-ALK V1 type.

As negative controls, PBMC cells and A549 cells (ATCC, CCL-185) were used. The composition of a qRT-PCR reaction mixture is shown in Table 2 below.

TABLE 2

| Composition of PCR reaction mixture | |
| --- | --- |
| Substances | Contents |
| 2X SYBR Green | 10 μl |
| Forward Primer | 1 μl |
| Reverse Primer | 1 μl |
| Template | 1 μl |
| Distilled water | 7 μl |
| Total volume | 20 μl |

PCR was performed under the following conditions: denaturation at 95° C. for 10 min, and then 40 cycles, each consisting of 30 sec at 95° C., 30 sec at 60° C., and 40 sec at 72° C., followed by extension at 72° C. for 10 min.

The PCR primers used were as follows:

```
EML4(E12)-FP:
                                       (SEQ ID NO: 1)
5'-CACACCTGGGAAAGGACCTA-3'
(V1 forward primer);

ALK(E20)-RP:
                                       (SEQ ID NO: 2)
5'-ACTACTGCTTTGCTGGCAAGACCT-3'
(V1 reverse primer);

Control primer sequence (FP):
                                       (SEQ ID NO: 5)
5'-GTGCAGTGTTTAGCATTCTTGGGG-3'
(forward primer);

Control primer sequence (RP):
                                       (SEQ ID NO: 6)
5'-ATCCAGTTCGTCCTGTTCAGAGC-3'
(reverse primer).
```

The qRT-PCR amplification products were electrophoresed on agarose gel to confirm the bands, and the confirmed bands were isolated and sequenced.

Figure 5:
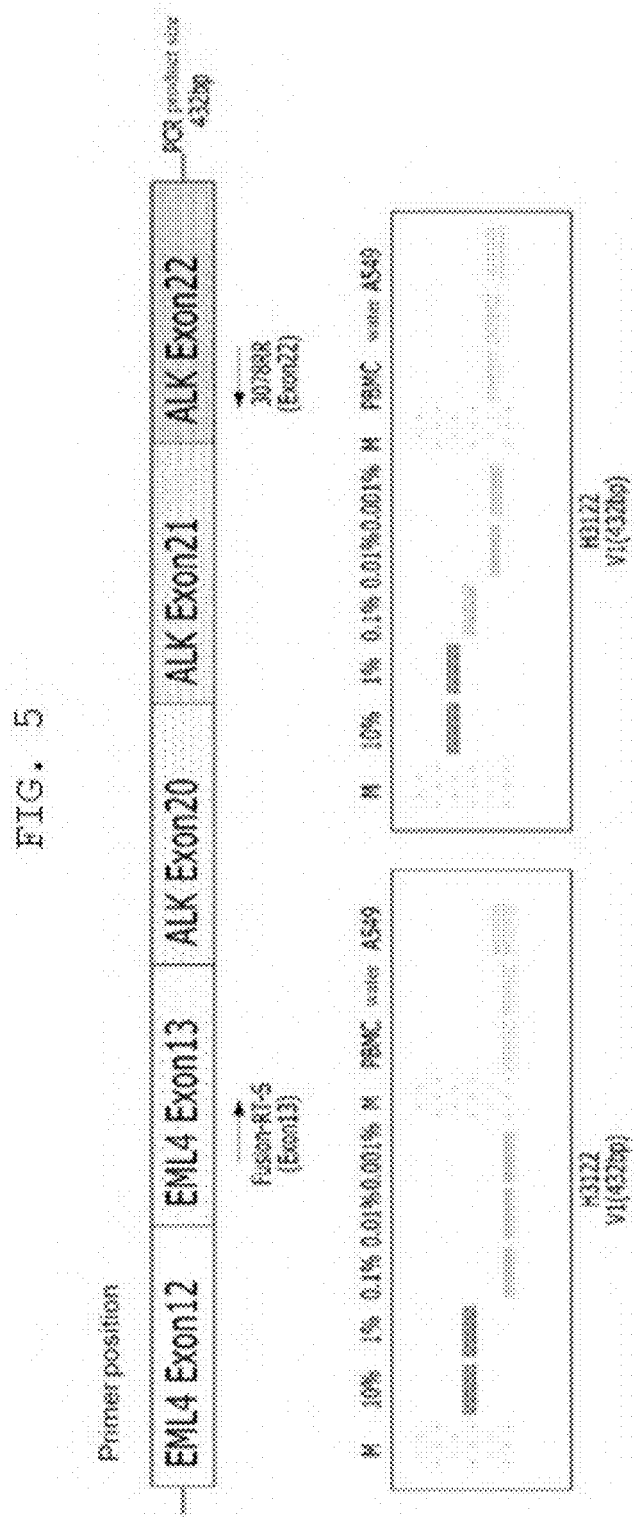
FIG. 5 shows the results of detecting EML4-ALK gene V1-type variant by a known method for detecting EML4-ALK gene V1 type.
Figure 6:
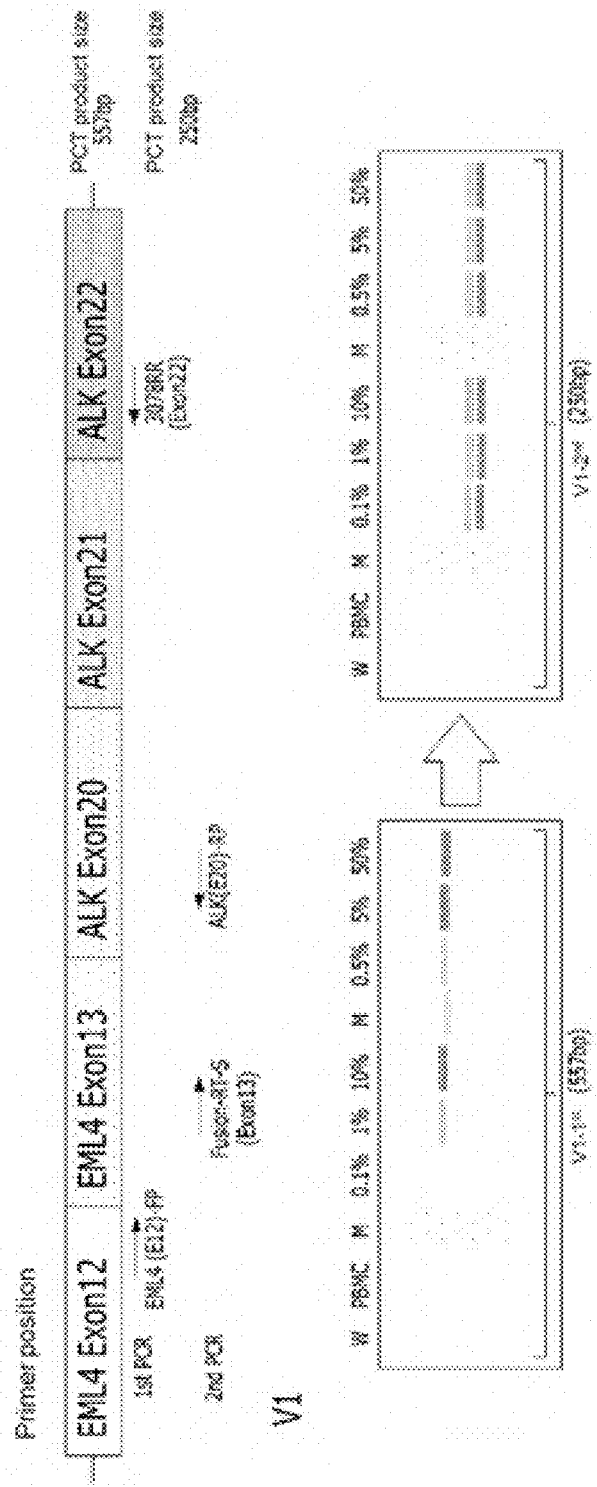
FIG. 6 shows the results of detecting EML4-ALK gene V1 type using EML4-ALK gene V1 type-detecting primers according to the present invention.

As a result, in both the PCR method (FIG. 5) performed using the known conventional primers and the qRT-PCR method (FIG. 6) performed using the primers of the present invention, the V1 variant could be detected at a detection limit of 0.1% to 1%, and in the method of the present Example, a clearer band could be confirmed. Here, 0.1% means that the variant can be detected in one circulating tumor cell per 1,000 white blood cells.

Example 6: Method of Detecting EML4-ALK V3-Type Variant by qRT-PCR

The H2228 cell line (ATCC, CRL-5935), a lung cancer cell line with EML4-ALK V3-type variant, was cultured, and then RNA was extracted therefrom. cDNA was synthesized from the extracted RNA, and the synthesized cDNA was diluted sequentially and used as a template in qRT-PCR template for detecting EML4-ALK V3 type. qRT-PCR was performed in the same manner as Example 5, except for the primers used.

qRT-PCR was performed using an EML4(E1E2)-FP primer (SEQ ID NO: 3) and an ALK(E20)-RP primer (SEQ ID NO: 2), a 789-bp (V3a type) or 822-bp (V3b type) PCR amplification product was obtained, and when qRT-PCR was performed using an EML4(E4)-FP primer (SEQ ID NO: 4) and an ALK(E20)-RP primer (SEQ ID NO: 2), a 387-bp (V3a type) or 420-bp (V3b type) qRT-PCR amplification product was obtained.

The qRT-PCR primers used were as follows.

```
EML4(E1E2)-FP:
                                       (SEQ ID NO: 3)
5'-CCAAAACTGCAGACAAGCAT-3'
(V3 forward primer);

EML4(E4)-FP:
                                       (SEQ ID NO: 4)
5'-CACAAATTCGAGCATCACCTTCTC-3'
(V3 forward primer);

ALK(E20)-RP:
                                       (SEQ ID NO: 2)
5'-ACTACTGCTTTGCTGGCAAGACCT-3'
(V3 reverse primer);

Control primer sequence (FP):
                                       (SEQ ID NO: 7)
5'-GTCAGCTCITGAGTCACGAGIT-3'
(forward primer);

Control primer sequence (RP):
                                       (SEQ ID NO: 8)
5'-ATCCAGITCGTCCTGITCAGAGC-3'
(reverse primer).
```

The qRT-PCR amplification products were electrophoresed on agarose gel to confirm the bands, and the confirmed bands were isolated and sequenced.

Figure 8:
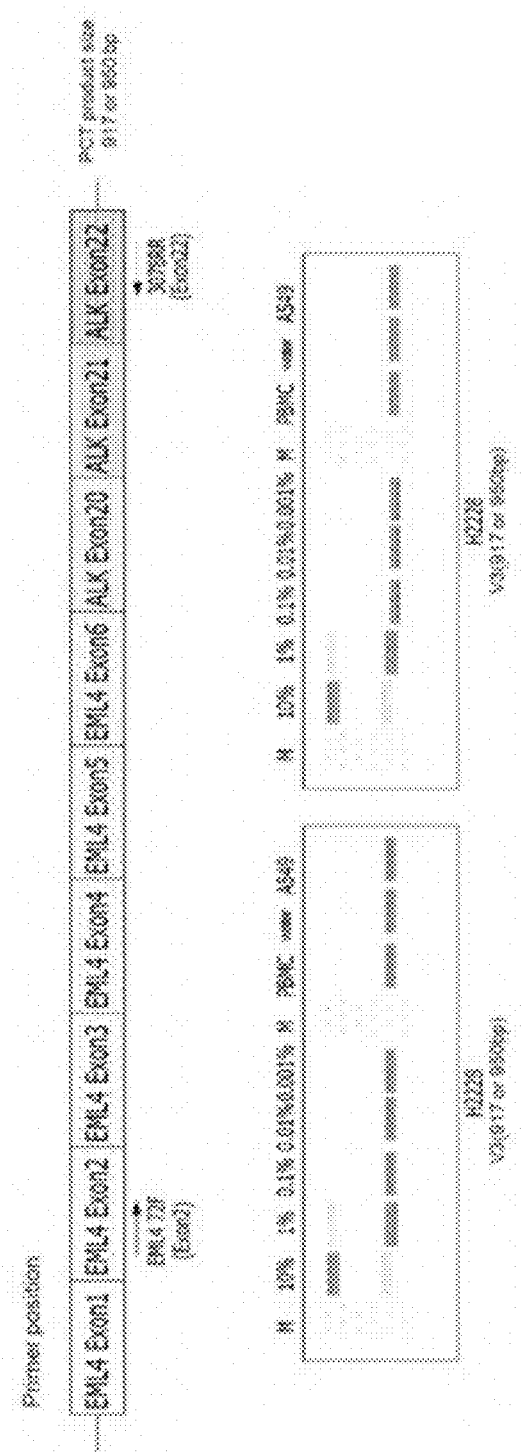
FIG. 8 shows the results of detecting EML4-ALK gene V3 variant by a known method for detecting EML4-ALK gene V3 type variant.
Figure 9:
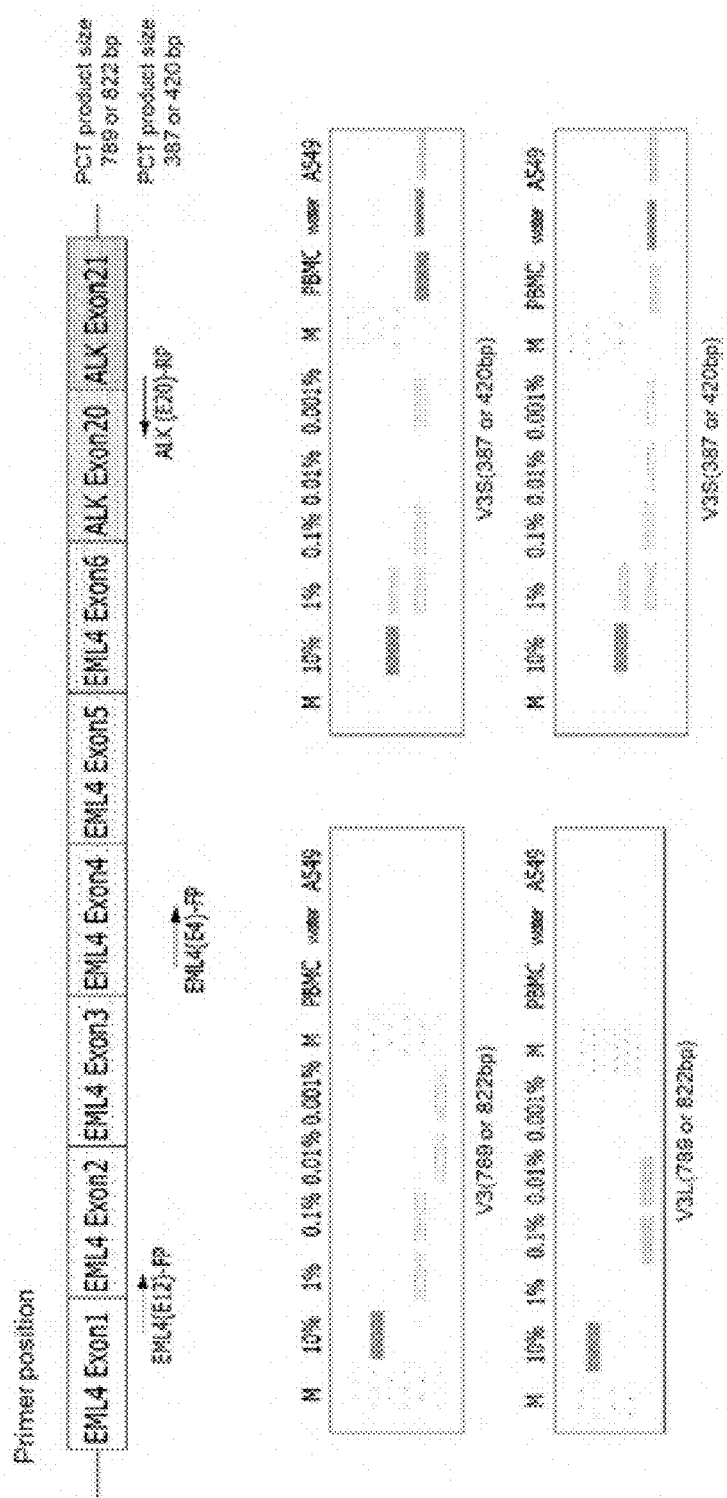
FIG. 9 shows the results of detecting EML4-ALK gene V3 type using EML4-ALK gene V3 type-detecting primers according to the present invention.

As a result, the PCR method (FIG. 8) performed using the known conventional primers could detect the V3 variant at a detection limit of 1% to 10%, and the PCR method (FIG. 9) performed using the primers of the present invention showed a detection limit of 1 to 10% when used the EML4(E1E2)-FP primer, and showed a detection limit of 0.1 to 1% when used the EML4(E4)-FP primer.

Example 7: Detection of V1 and V3 Type Variants by Nested PCR

In nested PCR for detection of the V1 variant, $1^{st}$ PCR was performed using an EML4(E12)-FP primer (SEQ ID NO: 1) and a 3078RR primer (SEQ ID NO: 9), and $2^{nd}$ PCR was performed using a fusion RT-S primer (SEQ ID NO: 10) and an ALK(E20)-RP primer (SEQ ID NO: 2).

```
3078RR primer sequence:
                                      (SEQ ID NO: 9)
5'-ATCCAGTTCGTCCTGTTCAGAGC-3';

Fusion RT-S primer sequence:
                                     (SEQ ID NO: 10)
5'-GTGCAGTGTTTAGCATTCTTGGGG-3'.
```

Figure 7:
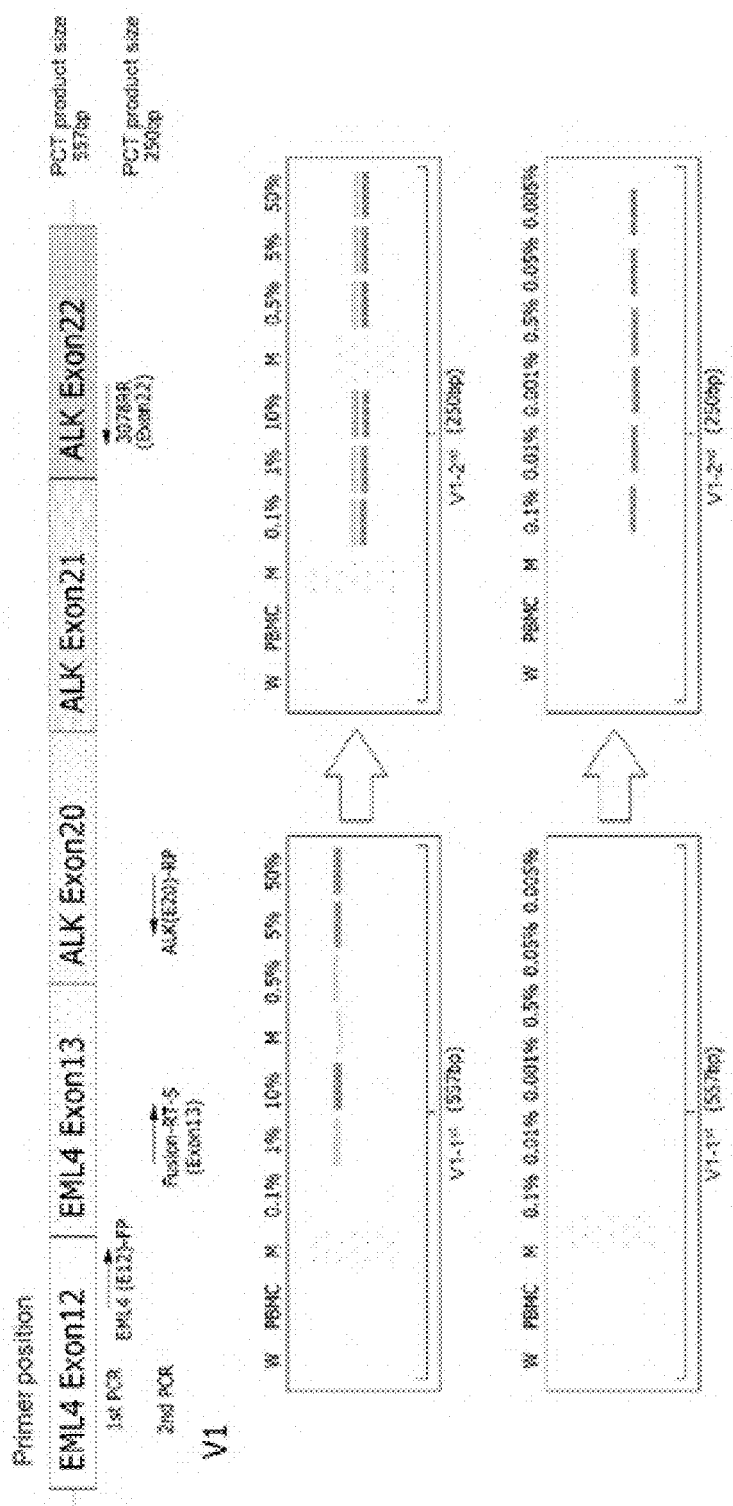
FIG. 7 shows the results of detecting EML4-ALK gene V1 type by performing nested PCR using EML4-ALK gene V1 type-detecting primers according to the present invention.

As a result, as shown in FIG. 7, it was confirmed that the V1 type variant could be detected at a detection limit of 0.001%, indicating that the sensitivity in the present invention was 1000-fold higher than that in the conventional art.

In nested PCR for detection of the V3 variant, $1^{st}$ PCR was performed using EML4(E1E2)-FP (SEQ ID NO: 3) and ALK(E20)-RP (SEQ ID NO: 2), and $2^{nd}$ PCR was performed using EML4(E4)-FP (SEQ ID NO: 4) and ALK (E20)-RP (SEQ ID NO: 2).

Figure 10:
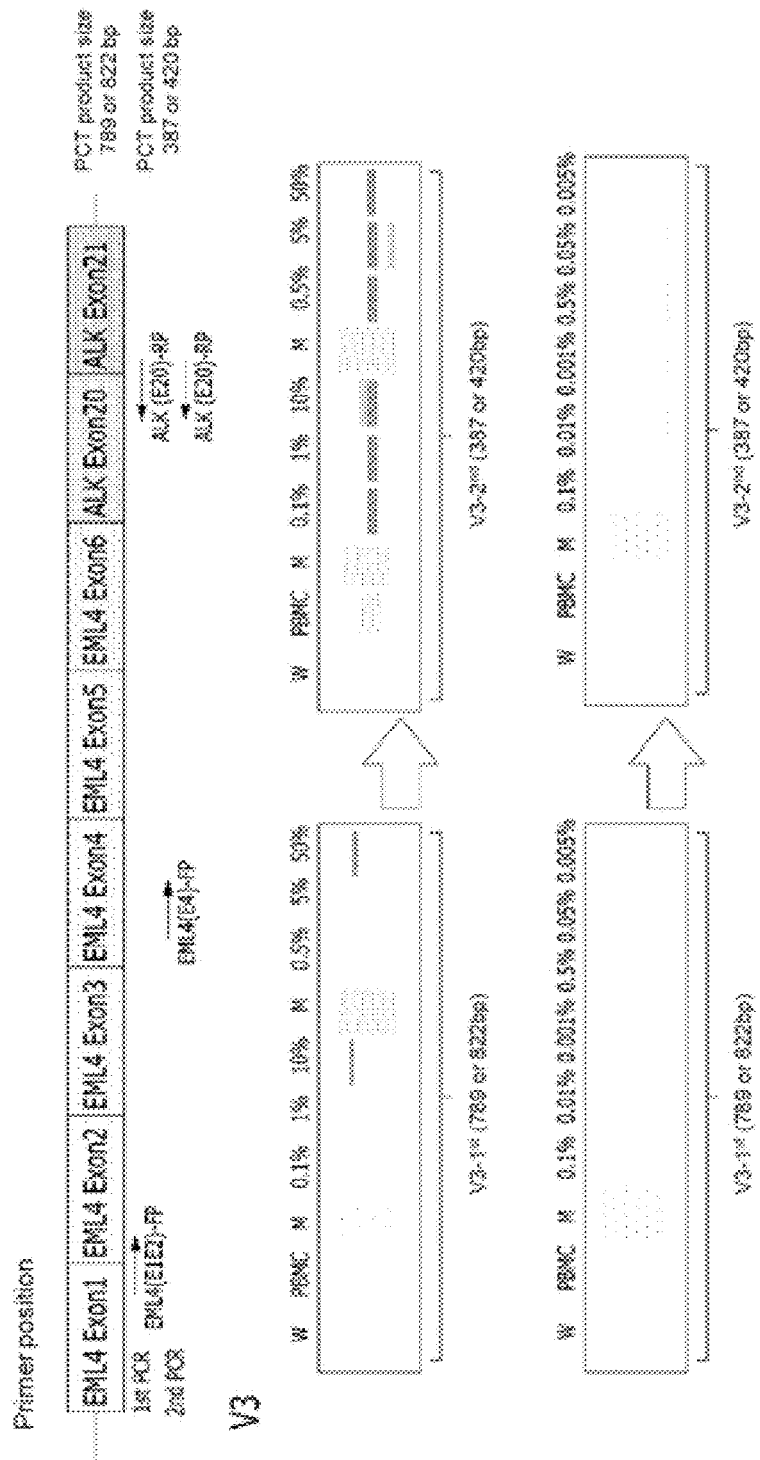
FIG. 10 shows the results of detecting EML4-ALK gene V3 type by performing nested PCR using EML4-ALK gene V3 type-detecting primers according to the present invention.

As a result, as shown in FIG. 10, it was confirmed that the V3 type variant could be detected at a detection limit of 0.1%, and the sensitivity was 10-fold higher.

Example 8: Detection of EML4-ALK Variant in Clinical Sample by Nested PCR

Using the PCR and nested PCR methods of Examples 6 and 7, EML4-ALK variant was detected in a clinical sample.

RNA was extracted from the blood of a patient (Seoul National University Hospital IRB 1209-029-424, Sep. 12, 2012) confirmed to be positive for EML4-ALK through the FISH result of cancer tissue among histologically confirmed non-small cell lung cancers. cDNA was synthesized from the extracted RNA, and nested PCR was performed using the synthesized cDNA as a template according to the method of Example 7.

Figure 11:
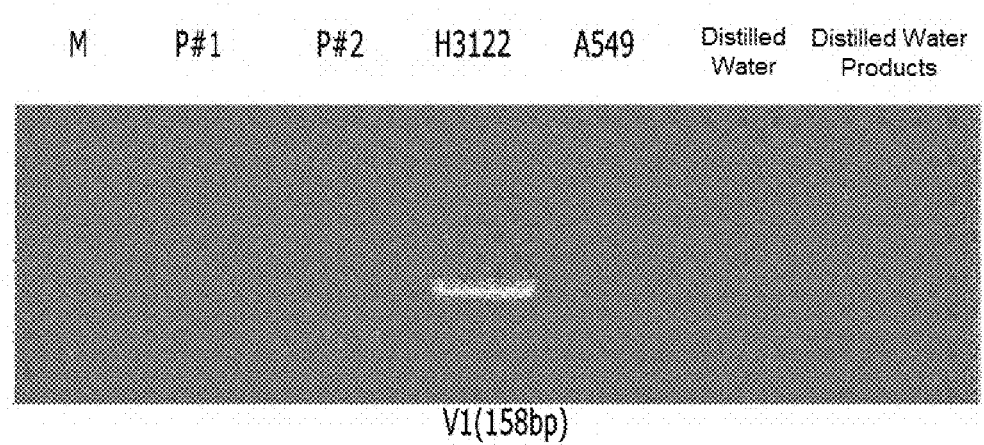
FIG. 11 shows the results obtained by applying EML4-ALK gene V1 type-detecting primers according to the present invention to an actual patient sample.
Figure 12:
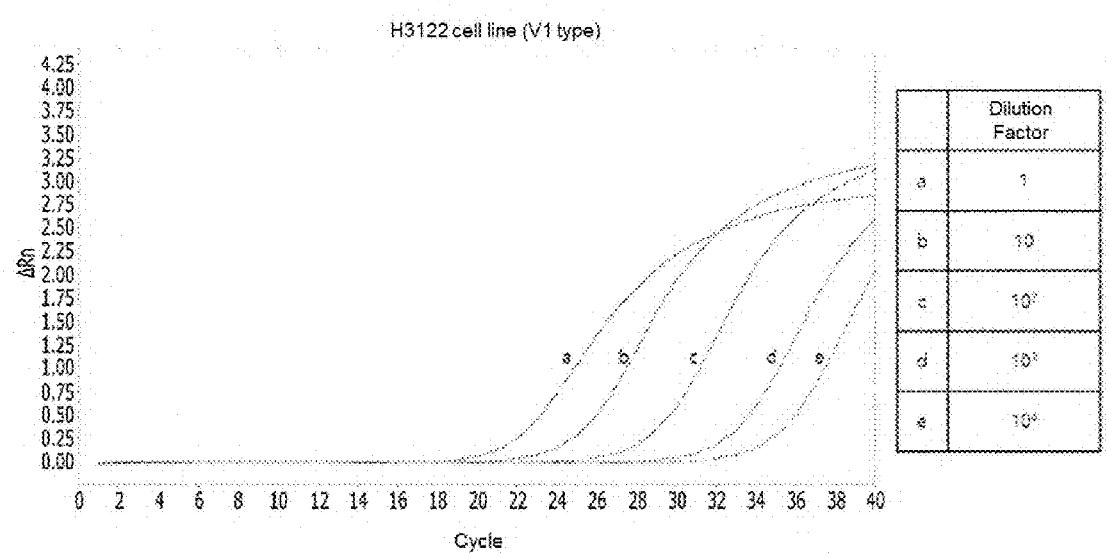
FIG. 12 shows a qRT-PCR graph of EML4-ALK gene V1 type in the H3122 cell line.
Figure 13:
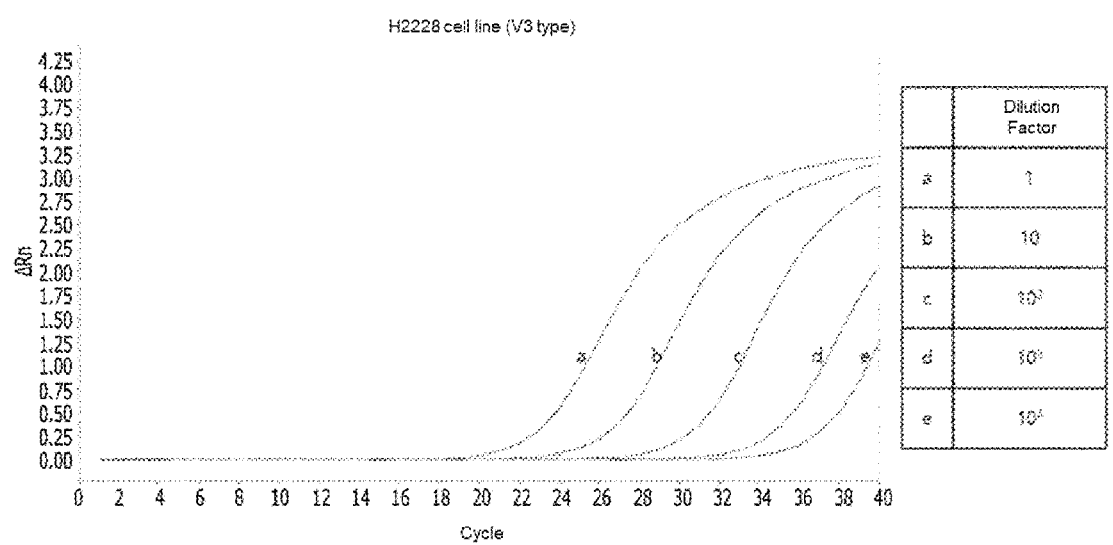
FIG. 13 shows a qRT-PCR graph of EML4-ALK gene V3 type in the H2228 cell line.

As a result, as shown in FIG. 11, it was confirmed that the V1 type variant was detected, indicating that EML4-ALK variant can be actually detected in the circulating tumor cells of a patient having the EML4-ALK variant.

The above description of the present invention is exemplary, and those of ordinary skill in the art will appreciate that the present invention can be easily modified into other specific forms without departing from the technical spirit or essential characteristics of the present invention. Therefore, it should be understood that the exemplary embodiments described above are exemplary in all aspects and are not restrictive. For example, each component described to be of a single type can be implemented in a distributed manner. Likewise, components described to be distributed can be implemented in a combined manner.

The scope of the present invention is defined by the claims described below. It shall be understood that all modifications and embodiments conceived from the meaning and scope of the claims and their equivalents are included in the scope of the present invention.

MODE FOR INVENTION

Hereinafter, the present invention will be described with reference to the accompanying drawings. However, the present invention may be embodied in various different forms, and thus is not limited to the embodiments described herein. In the drawings, parts irrelevant to the description are omitted for the simplicity of explanation, and like reference numerals designate like parts throughout the specification.

Throughout the specification, when any portion is referred to as being "connected, contacted or coupled" to another portion, this includes not only a case where any portion is "connected directly" to another portion but also a case where any portion is "connected indirectly" to another portion with one or more other elements interposed therebetween. In addition, it is understood that when any portion is referred to as comprising any component, it may further comprise one or more other components rather than excluding other components, unless otherwise specified.

Terms used in the present specification are only to describe specific embodiments and are not intended to limit the scope of the present invention. Singular expressions include plural expressions unless otherwise specified in the context thereof. In the present specification, it is to be understood that the terms "comprise", "have", etc., are intended to denote the existence of mentioned characteristics, numbers, steps, operations, components, parts, or combinations thereof, but do not exclude the probability of existence or addition of one or more other characteristics, numbers, steps, operations, components, parts, or combinations thereof.

Hereinafter, embodiments of the present invention will be described in detail with reference to the accompanying drawings.

A method for analyzing EML4-ALK gene variant according to one aspect of the present invention may comprise the steps of: (a) obtaining a liquid biopsy sample from a cancer patient; (b) isolating circulating tumor cells from the liquid biopsy sample using a biochip; (c) isolating RNA from the isolated circulating tumor cells; (d) performing qRT-PCR using the isolated RNA as a template and two qRT-PCR primers; (e) performing nested PCR using the resulting product from the qRT-PCR as a template and two nested primers for the two qRT-PCR primers; and detecting EML-ALK gene variant type based on the resulting product from the nested PCR.

The liquid biopsy refers to a test that samples cancer gene fragments from a bodily fluid, such as blood or ascites, without any invasive procedure such as puncture or incision. That is, the liquid biopsy enables detailed observation of cancer development and metastasis by analyzing cancer cell-derived DNA present in each body part's blood or ascites only by bodily fluid testing for blood or the like. According to one embodiment of the invention, the sample for the liquid biopsy may include blood, synovia, ascites, pleural fluid, cerebrospinal fluid, or peritoneal fluid. According to a preferred embodiment of the present invention, the liquid biopsy sample may be blood.

The circulating tumor cells (CTCs) mean tumor cells found in the peripheral blood of malignant tumor patients. The circulating tumor cells are very rare and the amount of samples available is very limited. Techniques for the detection and characterization of circulating cancer cells in blood include, but are not limited to, multiplex reverse transcriptase polymerase chain reaction methods, imaging-based approaches, microfiltration techniques and microchip devices. The circulating tumor cells are liquid biopsy samples and can act as tumor biomarkers that can inevitably provide individualized treatment and post-treatment follow-up. In addition, the circulating tumor cells may be used as targets for understanding the biological characteristics of tumors and the seeding of tumor cells, but are not limited thereto. According to one embodiment of the present invention, the circulating tumor cells may be lung cancer-derived cells. According to a preferred embodiment of the present invention, the circulating tumor cells may be cells derived from non-small cell cancer.

The biochip is a hybrid device made in an existing semiconductor chip form by integrating and combining substances, such as organism-derived DNA, proteins, enzymes, antibodies, microorganisms, animal and plant cells and organs, and neurons, on a solid substrate made of an inorganic material such as a semiconductor. The biochip refers to a tool or device that uses the inherent functions of biomolecules to obtain biological information, such as gene expression patterns, gene binding or protein distributions, or speeds up biochemical processes and reactions or information processing.

The high-density microporous chip refers to a biochip capable of isolating a substance having a specific size based on the working principle of the biochip.

The high-density microporous is based on the size difference of blood cells and can capture circulating tumor cells with a recovery rate of about 90% within 10 minutes.

In an embodiment of the present invention, the pore size of the high-density microporous chip may preferably be 5.5 to 8.5 µm, more preferably 6.5 to 7.5 µm. If the pore size is smaller than 5.5 µm, red blood cells and white blood cells cannot be removed, because these cells remain on the chip without passing through the chip, and if the pore size is larger than 8.5 µm, circulating tumor cells and immune cells cannot be selectively recovered, because the pore size is larger than the size of circulating tumor cells and immune cells and these circulating tumor cells and immune cells pass through the chip. In one embodiment of the present invention, the pore shape of the high-density microporous chip may be circular, rectangular or elliptic, and preferably rectangular.

In one embodiment of the present invention, the pores of the high-density microporous chip may be arranged in a regular pattern. In another embodiment of the present invention, the high-density microporous chip may be specifically made of stainless steel, nickel, aluminum, or copper. The pores may be formed by etching using MEMS (Micro-electro Mechanical Systems) technology.

The spacing between two adjacent pores of the pores is narrower than the diameter of circulating tumor cells and immune cells. According to one embodiment of the invention, the spacing between the two pores may be 45 to 65% relative to the diameter of circulating tumor cells and immune cells. The high-density microporous chip is not deformed by the pressure of the blood or solution flowing through the channel.

After passing through the pores, the blood is discharged to the outside and the circulating tumor cells in the blood remain on the surface without passing through the pores. According to one embodiment of the present invention, the circulating tumor cells may be lung cancer-derived cells. According to a preferred embodiment of the present invention, the circulating tumor cells may be non-small cell lung cancer-derived cells.

Non-target cells, that is, red blood cells having a higher deformation rate than the circulating tumor cells, easily pass through the pores.

After filtration of the circulating tumor cells, the circulating tumor cells may be discharged to the outside by supplying a solution in the reverse or forward direction. According to one embodiment of the present invention, the solution may be supplied in the reverse direction to minimize damage to the circulating tumor cancer cells. The solution may be supplied by a syringe, a syringe pump, a plunger pump, or the like. According to one embodiment of the present invention, the solution may be composed of a diluent, water and diluent acid, which dilute the blood. The circulating tumor cells and immune cells discharged to the outside by supplying the solution may be easily collected in a container, for example, a test tube or a culture dish.

Meanwhile, circulating tumor cells having a diameter of 7.5 to 15 µm pass through a tube having a diameter of 8 µm when a pressure of about 100 mmHg is applied thereto. Circulating tumor cells having a diameter of 15 µm, which pass through the 8-µm diameter tube, have a deformation rate of about 53%. The spacing between two pores is preferably 4 µm or less in consideration of the deformation rate of the circulating tumor cells when the circulating tumor cells having a diameter of 7.5 µm are discharged to the outside by back washing, i.e., allowing the solution to flow in a direction opposite to the flow of the blood. Non-small cell lung cancer and breast cancer cells, for example, are known to have a diameter reaching about 40 µm. In consideration of the deformation rate of circulating cancer cells having a diameter of 40 µm during back washing, the spacing between two pores is preferably set to 21 µm or less. When circulating cancer cells having a diameter of 7.5 µm are present between two pores having a spacing larger than 4 µm, the circulating tumor cells may not be detached from the surface as they are deformed by the flow of the solution. In addition, tumor cells having a diameter of 40 µm may also not be detached from the surface between two pores having a spacing larger than 21 µm. In the high-density microporous chip according to the present invention, the spacing between two pores is 45 to 65% of the diameter of the circulating tumor cells in consideration of the pressure of the solution. If the spacing is larger than 65%, that is, larger than about 4.9 µm, circulating cancer cells having a diameter of 7.5 µm may not be detached from the surface between the two pores by back washing. If the spacing is larger than 65%, that is, larger than 26 µm, circulating tumor cells having a diameter of 40 µm may not be detached from the surface between two pores by back washing. If the pressure of the solution is increased to forcibly detach the circulating tumor cells attached to the surface between two pores, damage to the circulating tumor cells may occur, which reduces the collection rate of living circulating tumor cells. If the spacing for circulating cancer cells having a diameter of 7.5 µm is less than 45%, that is, smaller than about 3.375 µm, the high-density microporous chip is highly likely to be damaged by the flow of the blood and the solution.

In one embodiment of the present invention, the sample may be repeatedly passed through the high-density microporous chip. Specifically, after circulating tumor cells are isolated once from the high-density microporous chip, the isolated circulating tumor cells may be loaded again onto the high-density microporous chip and isolated, and the isolation process may be repeated.

In one embodiment of the present invention, isolation of the circulating tumor cells through the high-density microporous chip is not performed by applying a specific artificial pressure after loading the solution containing the circulating tumor cells onto the high-density microporous chip, but may be performed using gravity. Isolation of circulating tumor cells through the high-density microporous chip according to the present invention may minimize damage caused to the circulating tumor cells by artificial pressure, thereby maintaining the circulating tumor cells at the same state as when these cells are present in the body of the patient.

In one embodiment of the present invention, the high-density microporous chip may be coated with a specific material in order to minimize damage caused to the circulating tumor cells by the high-density microporous chip during isolation of the circulating tumor cancer cells, or to make the repeated use of the high-density microporous chip more efficient, or to make recovery of the circulating tumor cells more efficient. Specifically, the specific material may be an antibody that can bind specifically to the circulating tumor cells, and may be any biomaterial that does not physically or chemically damage the cells. According to one embodiment of the present invention, the specific material may be BSA (bovine serum albumin) or an antibody. The antibody may be composed of, for example, an anti-epithelial cell adhesion molecule antibody (anti-EpCAM antibody), an anti-cytokeratin antibody (anti-CK antibody), or the like. According to a preferred embodiment of the present invention, the specific material may be BSA (bovine serum albumin).

The BSA (bovine serum albumin) solution refers to bovine serum albumin. It is a protein having a molecular weight of about 66.4 kDa, which is abundantly found in most animals. BSA may be added as a nutrient to cells during cell culture in biochemistry/biology, and is also frequently used as a standard for obtaining a calibration curve in protein quantification. In addition, since a small amount of enzyme (protein) needs to be used when a restriction enzyme is used, BSA may also be added to compensate for the concentration of the protein in a solution. In addition, in various biochemical experiments (Western blotting, immunocytochemistry, ELISA, etc.), BSA may also be used to prevent nonspecific binding, that is, prevent a specific antibody from binding to an unwanted protein or an unwanted position, before the specific antibody is attached to a protein to be detected.

According to one embodiment of the present invention, centrifugation may be used to allow peripheral blood to react with the high-density microporous chip coated with the BSA solution, thereby removing biopolymers other than the circulating tumor cells. According to one embodiment of the present invention, the isolation using the high-density microporous chip may be performed using gravity. Specifically, the isolation may be performed under atmospheric pressure of 1000 hPa to 1020 hPa. Preferably, it may be performed under atmospheric pressure of 1000 hPa to 1015 hPa. More preferably, it may be performed under atmospheric pressure of 1000 hPa to 1013 hPa.

According to one embodiment of the present invention, the BSA solution may be coated on the upper surface or lower surface of the high-density microporous chip or the inner surface of the pores. Preferably, the BSA solution may be coated on all the upper surface and lower surface of the high-density microporous chip and the inner surface of the pores.

According to one embodiment of the present invention, the BSA solution coating may be performed at a BSA concentration of 0.05 to 0.15%. According to a preferred embodiment of the present invention, the BSA solution coating may be performed at a BSA concentration of 0.08 to 0.012%.

According to one embodiment of the present invention, the BSA solution coating may be performed for 5 to 15 minutes. According to one preferred embodiment of the present invention, the BSA solution coating may be performed for 8 to 12 minutes.

Referring to FIG. 1, in order to first remove blood cells from patient's blood, an antibody polymer is added to collected patient's blood and then mixed well, followed by reaction at room temperature. Thereafter, a PBS solution containing 1% FBS is added, Ficoll solution is placed on the reaction solution, and then the blood cells are primarily removed by centrifugation. After the blood cells which are unnecessary in the present invention are primarily removed as describes above, red blood cells are filtered out using the high-density microporous chip specially coated with the BSA solution, thereby isolating highly pure circulating tumor cells. The isolated circulating tumor cells are identified by staining. When the high-density microporous chip coated with BSA is used, the circulating tumor cells to be isolated in the present invention may be isolated with minimal damage to the circulating tumor cells. These highly pure circulating tumor cells can significantly increase the efficiency so that the method for analyzing EML4-ALK gene variant according to the present invention works effectively.

According to one embodiment of the present invention, after the step of isolating the circulating tumor cells from the liquid biopsy sample by using the biochip, a step of performing short-term culture of the isolated circulating tumor cells may further be performed.

In one embodiment of the present invention, a culture medium that is used in the short-term culture may be composed of at least three selected from the group consisting of insulin, transferrin, EGF (epidermal growth factor) and an ROCK (Rho kinase) inhibitor.

The insulin is one of human metabolic hormones, is secreted from the Langerhans Island beta cells of the pancreas (organ) and serves to maintain the blood glucose level at a constant level. When the blood sugar level rises above a certain level, insulin is secreted and promotes the action of introducing blood glucose into cells and storing it again in the form of polysaccharide (glycogen). As the culture medium that is used in the short-term culture step according to the present invention contains insulin, it may further promote cell growth and division during culture of circulating tumor cells compared to a conventional culture medium for culturing circulating tumor cells. According to one embodiment of the present invention, the content of the insulin may be 3 to 50 ng/ml, 3 to 45 ng/ml, 3 to 40 ng/ml, 3 to 30 ng/ml, 4 to 50 ng/ml, 4 to 45 ng/ml, 4 to 30 ng/ml, 5 to 50 ng/ml, 5 to 45 ng/ml, or 5 to 30 ng/ml.

The transferrin, a kind of β-globulin, is an iron-transporting protein that binds to trivalent iron ions of two molecules absorbed in serum and supplies iron necessary for cell proliferation or hemoglobin production to cells through transferrin receptor. More than 99% of iron in serum binds to transferrin, and normally about one third of transferrin can bind to iron. As the culture medium that is used in the short-term culture step according to the present invention contains the transferrin, it can further promote cell growth and division in the culture of circulating tumor cells compared to a conventional culture medium for culturing circulating tumor cells. According to one embodiment of the present invention, the content of the transferrin may be 3 to 50 ng/ml, 3 to 45 ng/ml, 3 to 40 ng/ml, 3 to 30 ng/ml, 4 to 50 ng/ml, 4 to 45 ng/ml, 4 to 30 ng/ml, 5 to 50 ng/ml, 5 to 45 ng/ml, or 5 to 30 ng/ml.

The epidermal growth factor (EGF) is a polypeptide growth factor that binds to epidermal growth factor receptor and promotes cell growth and division. In addition, the epidermal growth factor may induce ornithine decarboxylase in addition to promoting protein synthesis and RNA synthesis. As the culture medium that is used in the short-term culture step according to the present invention contains the epidermal growth factor, it may further promote cell growth and division in the culture of circulating tumor cells compared to a conventional culture medium for culturing circulating tumor cells. According to an embodiment of the present invention, the content of the epidermal growth factor may be 0.5 to 10 ng/ml, 0.5 to 9 ng/ml, 0.5 to 8 ng/ml, 0.5 to 7 ng/ml, 0.5 to 6 ng/ml, 0.5 to 5 ng/ml, 0.7 to 10 ng/ml, 0.7 to 9 ng/ml, 0.7 to 8 ng/ml, 0.7 to 7 ng/ml, 0.7 to 6 ng/ml, 0.7 to 5 ng/ml, 1 to 10 ng/ml, 1 to 9 ng/ml, 1 to 8 ng/ml, 1 to 7 ng/ml, 1 to 6 ng/ml, or 1 to 5 ng/ml.

The Rho-associated protein kinase (ROCK) inhibitor refers to a compound capable of capable of targeting Rho kinase (ROCK) and inhibiting or decreasing its function. Here, Rho kinase is a kinase belonging to the AGC family of serine-threonine kinases (PKA/PKG/PKC). The Rho kinase is involved in the process of controlling the movement and morphology of cells by acting on cytoskeleton. Specifically, the Rho kinase may act as a regulator of cell migration and actin organization. The Rho kinase is related to neurodegenerative diseases such as diabetes, hemorrhagic cerebrovascular disease, and Parkinson's disease, and the Rho kinase inhibitor can be used for the treatment and suppression of the Rho kinase-related diseases. According to one embodiment of the present invention, the ROCK inhibitor may be at least one selected from the group consisting of Fasudil, Ripasudil, RKI-1447 and Y27632. The Fasudil is one of ROCK inhibitors, and may be used for the treatment of cerebrovascular spasm and may also be effective in treating pulmonary hypertension. The Ripasudil, a derivative of the Fasudil, may act as a ROCK inhibitor and may also be used for the treatment of glaucoma or ocular hypertension. The RKI-1447 can suppress ROCK1 and ROCK2. The Y27632 can pass through cells and suppress ROCK1 and ROCK2 by competing with ATP for binding the catalytic site of enzyme. According to one embodiment of the present invention, the ROCK inhibitor may be 3 to 30 µM, 3 to 27 µM, 3 to 24 µM, 3 to 21 µM, 4 to 20 µM, 4 to 30 µM, 4 to 27 µM, 4 to 24 µM, 4 to 21 µM, 4 to 20 µM, 5 to 30 µM, 5 to 27 µM, 5 to 24 µM, 5 to 21 µM, or 5 to 20 µM.

The culture plate that is used in the short-term culture according to the present invention may have a surface that prevents cell adhesion. According to one embodiment of the present invention, the circulating tumor cells may be cultured in a suspended state, and hence the surface of the culture plate may be coated to prevent cell adhesion. The surface of the culture plate may be coated with a hydrogel. The hydrogel refers to a gel containing water as a dispersion medium, and is formed when hydrosol loses its fluidity due to cooling or when a hydrophilic polymer having a three-dimensional network structure and a microcrystalline structure is swollen by water contained therein. Specifically, the hydrogel is a hydrophilic polymer crosslinked by interactions such as covalent bonds, hydrogen bonds, van der Waals bonds or physical bonds, and is a material having a three-dimensional polymer network structure capable of swelling in an aqueous solution by a large amount of water contained therein. In a state in which the hydrogel absorbed water as described above, it shows a behavior similar to that of a living body tissue. The hydrogel may undergo a phase transition with a change in temperature, pH or the like, and hence the swelling rate thereof may discontinuously change. The hydrogel may be used for contact lenses, medical electrodes, and cell culture. According to one embodiment of the present invention, the hydrogel may be covalently coated on the culture plate and can prevent the circulating tumor cells from adhering to the surface of the culture plate. According to another embodiment of the present invention, the hydrogel may have hydrophilicity while having a neutral charge. The expression "having the neutral charge" means that the charge is neither positive nor negative, and the term "hydrophilicity" refers to a strong affinity for water, and means that the hydrogel can be easily dissolved in water.

In one embodiment of the present invention, the short-term culture step may be performed for 1 to 15 days from the start of the culture. In another embodiment of the present invention, it may be performed for 5 to 15 days, preferably 10 to 15 days. Even more preferably, it may be performed for 12 to 15 days.

According to one embodiment of the present invention, ALK-positive non-small cell lung cancer is lung cancer caused by the EML4-ALK variant created by the fusion of two genes (ALK and EML4), and the EML4-ALK variant has various variant types as indicated below depending on the exon or intron sites of the EML4 gene fused.

Variant 1: exons 1 to 13 (EML4)+exons 20 to 29 (ALK);
Variant 2: exons 1 to 20 (EML4)+exons 20 to 29 (ALK);
Variant 3a: exons 1 to 6a (EML4)+exons 20 to 29 (ALK);
Variant 3b: exons 1 to 6b (EML4)+exons 20 to 29 (ALK);
Variant 4a: exon 15 (EML4)+exons 20 to 29 (ALK);
Variant 4b: exon 14 (EML4)+a linker consisting of a 11-bp oligonucleotide+exons 20 to 29 (ALK);
Variant 5a: exon 2 (EML4)+exons 20 to 29 (ALK);
Variant) 5b: exon 2 (EML4)+intron 19 (ALK)+exon 20-29 (ALK).

Among these variants, patients with two variant types (variant 1 (V1) and variant 3 (V3)) were found to be dominant in Korea. It was reported that when 167 patients with non-small cell lung cancer were examined, 10 patients had EML4-ALK fusion variants, and among them, 4 patients had V1 type variant and two patients had V3b type variant (*J. Korean Med. Sci.,* 27:228-230, 2012).

The V3 type includes two isoforms, and the V3b type additionally includes 33 bp of EML4 intron 6 in the fusion portion. Thus, when the V3 type is detected by PCR, PCR products with two different sizes may occur.

According to one embodiment of the present invention, the EML4-ALK gene variant type may be V1 type, V2 type, V3a type, V3b type, V4a type, V4b type, V5a type or V5b type, preferably V1 type or V3 type.

The step of isolating the RNA may be performed according to a method which is commonly used in the art, and may be performed using a commercially available RNA extraction kit. In addition, in the step of performing qRT-PCR, qRT-PCR may comprise synthesizing a complementary DNA strand by a reverse transcriptase reaction using the isolated RNA as a template and a reverse qRT-PCR primer among the two qRT-PCR primers of the present invention, and then performing a PCR reaction. The PCR reaction may be performed using a PCR reaction mixture containing various components known in the art, which are necessary for the PCR reaction. The PCR reaction mixture contains, in addition to the complementary DNA synthesized by the reverse transcriptase reaction and the qRT-PCR primers provided in the present invention, suitable amounts of DNA polymerase, dNTP, PCR buffer solution and distilled water (dH$_2$O). The PCR buffer solution contains Tris-HCl, MgCl$_2$, KCl, and the like. At this time, the concentration of MgCl$_2$ significantly affects the specificity and quantity of amplification. Generally, when Mg$^{2+}$ is excessive, a nonspecific PCR amplification product increases, and when Mg$^{2+}$ is insufficient, the yield of a PCR product decreases. The PCR buffer solution may further contain a suitable amount of Triton X-100. In addition, the PCR may be performed under the following normal PCR reaction conditions: a number of cycles, each consisting of denaturation, annealing and extension, and then final elongation at 72° C. The denaturation and the extension may be performed at 94 to 95° C. and 72° C., respectively, and the temperature of the annealing may change depending on the kind of primer. According to the present invention, the annealing may be performed at 55 to 64° C. for the qRT-PCR primers of the present invention. The time of each stage and the number of the cycles may be determined according to conditions which are generally used in the art.

The detection limits of known primers which have been used for the detection of EML4-ALK variant are 0.1 to 1%, and if a sample is cancer tissue, there is no problem in the detection of the variant. However, in order to use the method of isolating circulating tumor cells and detecting the variant, the variant should be capable of being detected even at a detection limit of 0.1% or lower, and hence primers with a low detection limit are necessary. In the present invention, in order to design primers having high accuracy and detection efficiency, primers were designed in the following manner. For primer design, candidates were determined using primer3 (http://bioinfo.ut.ee/or imer3-0.4.0/) primer design program, and then Blast search in NCBI homepage (htto://www.ncbi.nlm.nih.gov/) was performed to avoid the possibility of primer binding to regions other than the EML4-ALK region and the possibility of occurrence of hairpin structures. In addition, direct comparison of homology between primers was performed to prevent the formation of a dimer between the primers, and the GC content of the primers was checked so that it did not exceed 60% or more. The Tm values of the four primers were adjusted to similar values so that PCR could be easily performed even when any combination of the primers was used. The occurrence of repeated or contiguous sequences was avoided, and because cDNA would be used as a template, the primers were designed between the junctions between exons in order to prevent the primers from binding to genomic DNA, resulting in multiple bands.

According to another embodiment of the present invention, one of the two qRT-PCR primers may be one forward qRT-PCR primer selected from the group consisting of primers represented by SEQ ID NO: 1, SEQ ID NO: 3 and SEQ ID NO: 4, and the other may be composed of a reverse qRT-PCR primer represented by SEQ ID NO: 2.

According to one embodiment of the present invention, the two qRT-PCR primers may be selected from the group consisting of a primer pair represented by SEQ ID NO: 1 and SEQ ID NO: 2; a primer pair represented by SEQ ID NO: 3 and SEQ ID NO: 2; and a primer pair represented by SEQ ID NO: 4 and SEQ ID NO: 2.

According to another embodiment of the present invention, a pair of the two qRT-PCR primers represented by SEQ ID NO: 1 and SEQ ID NO: 2 may be used to detect the EML4-ALK V1 type gene variant, and the primer pair represented by SEQ ID NO: 3 and SEQ ID NO: 2, and the primer pair represented by SEQ ID NO: 4 and SEQ ID NO: 2 may be used to detect the EML4-ALK V3 type gene variant.

In the step of performing the nested PCR, the PCR product DNA may be separated by size according to a method widely known in the art. Preferably, the PCR product may be analyzed by agarose gel or polyacrylamide gel electrophoresis or a fluorescence analysis device (ABI prism 3100 genetic analyzer-electropherogram). At this time, to use the fluorescence analysis device, PCR is performed in the step of performing the qRT-PCR using two qRT-PCR primers labeled with two dyes known in the art. In addition, the nested PCR step may further minimize the errors caused nonspecific binding in the detection of PCV, and thus may be usefully used when necessary.

The results of PCR amplification may preferably be analyzed by agarose gel electrophoresis. After electrophoresis, the electrophoresis results may be analyzed by ethidium bromide staining. The normal reverse transcriptase reaction, the method of performing the PCR reaction and the method of analyzing the results of the PCR are well known in the art.

According to one embodiment of the present invention, one of the two nested primers may be a forward nested primer, and the other may be a reverse nested primer.

According to one embodiment of the present invention, one of the two nested primers may be one forward nested primer selected from the group consisting of primers represented by SEQ ID NO: 1, SEQ ID NO: 3, SEQ ID NO: 4 and SEQ ID NO: 10, and the other may be one reverse nested primer selected from the group consisting of SEQ ID NO: 2 and SEQ ID NO: 9. However, any primer pair capable of amplifying the qRT-PCR product may be used without limitation.

According to other embodiments of the present invention, a pair of the two nested primers represented by SEQ ID NO: 1 and SEQ ID NO: 9, and the primer pair represented by SEQ ID NO: 10 and SEQ ID NO: 2 may be used to detect the EML4-ALK V1 type gene variant, and the primer pair represented by SEQ ID NO: 3 and SEQ ID NO: 2, and the primer pair represented by SEQ ID NO: 4 and SEQ ID NO: 2 may be used to detect the EML4-ALK V3 type gene variant.

The standard recombinant DNA and molecular cloning techniques used in the present invention are widely known in the art and are described in Sambrook, J., Fritsch, E. F. and Maniatis, T., Molecular Cloning: A LaboratoryManual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N Y (1984); and by Ausubel, F. M. et al., Current Protocols in Molecular Biology, published by Greene Publishing Assoc. and Wiley-Interscience (1987).

A method for screening a cancer patient according to another aspect of the present invention may indicate that if the cancer patient's gene variant obtained through the method for analyzing EML4-ALK gene variant corresponds to one selected from the group consisting of (i) exons 1 to 13 of the EML4 gene+exons 20 to 29 of the ALK gene;

(ii) exons 1 to 20 of the EML4 gene+exons 20 to 29 of the ALK gene;

(iii) exons 1 to 6a of the EML4 gene+exons 20 to 29 of the ALK gene;

(iv) exons 1 to 6b of the EML4 gene+exons 20 to 29 of the ALK gene;
(v) exon 15 of the EML4 gene+exons 20 to 29 of the ALK gene;
(vi) exon 14 of the EML4 gene+a linker composed of a 11-bp oligonucleotide+exons 20 to 29 of the ALK gene;
(vii) exon 2 of the EML4 gene+exons 20 to 29 of the ALK gene; and
(viii) exon 2 of the EML4 gene+intron 19 of the ALK gene+exons 20 to 29 of the ALK gene,
an anticancer drug is effective for the cancer patient.

According to one embodiment of the present invention, the cancer may be lung cancer, preferably non-small cell lung cancer.

According to another embodiment of the present invention, the anticancer agent may be crizotinib.

A targeted anticancer drug for non-small cell lung cancer caused by EML4-ALK variants is crizotinib (product name: XALKORI, Pfizer). At present, the treatment of non-small cell lung cancer is performed by testing EGFR gene variants and EML4-ALK fusion variants and then selecting a therapeutic method from among Iressa, Xalkori and a conventional cytotoxic anticancer agent.

However, in the case of patients on whom invasive biopsy for lung tissue was impossible, genetic testing for EML4-ALK fusion variants could not be performed, and hence the effectiveness of administration of crizotinib could not be confirmed, and thus treatment by administration of crizotinib could not be performed.

The method for screening a cancer patient according to the present invention may determine the effectiveness of crizotinib for a non-small cell lung cancer patient by isolating circulating tumor cells from the blood of the non-small cell lung cancer patient and detecting the presence of EML4-ALK fusion variant in the circulating tumor cells.

Hereinafter, examples of the present invention will be described in detail so that those skilled in the art can easily carry out the present invention. However, the present invention may be embodied in various different forms and is not limited to the examples described herein.

The invention claimed is:

1. A method for analyzing EML4-ALK gene variant comprising the steps of:
(a) obtaining a liquid biopsy sample from a cancer patient;
(b) isolating circulating tumor cells from the liquid biopsy sample using a biochip;
(c) performing short-term culture of the isolated circulating tumor cells in the step (b);
(d) isolating RNA from the short-term cultured circulating tumor cells in the step (c);
(e) performing qRT-PCR using the isolated RNA as a template and two qRT-PCR primers;
(f) performing nested PCR using a resulting product from the qRT-PCR as a template and two nested primers for the two qRT-PCR primers; and (g) detecting EML4-ALK gene variant type based on the resulting product from the nested PCR, wherein the biochip is a high-density microporous chip coated with a BSA solution, wherein the high-density microporous chip is a size-based chip, wherein a pore size of the high-density microporous chip is 5.5 to 8.5 μm, wherein the circulating tumor cells in the step (b) is isolated by gravity, wherein the culture medium used in the short-term culture is consisting of insulin, transferrin, epidermal growth factor (EGF) and an Rho kinase (ROCK) inhibitor, and wherein the culture plate used in the short-term culture is coated with hydrogel.

2. The method of claim 1, wherein the liquid biopsy sample is blood.

3. The method of claim 1, wherein the cancer is lung cancer.

4. The method of claim 1, wherein the cancer is non-small cell lung cancer.

5. The method of claim 1, wherein the step of isolating the circulating tumor cells is performed under atmospheric pressure of 1000 hPa to 1020 hPa.

6. The method of claim 1, wherein the coating with a BSA solution is performed at a BSA concentration of 0.05 to 0.15%.

7. The method of claim 1, wherein the EML4-ALK gene variant type is V1 type or V3 type.

8. The method of claim 1, wherein one of the two qRT-PCR primers is a forward qRT-PCR primer and the other is a reverse qRT-PCR primer.

9. The method of claim 8, wherein the forward qRT-PCR primer is one selected from the group consisting of SEQ ID NO: 1, SEQ ID NO: 3 and SEQ ID NO: 4.

10. The method of claim 8, wherein the reverse qRT-PCR primer is SEQ ID NO: 2.

11. The method of claim 1, wherein one of the two nested primers is a forward nested primer and the other is a reverse nested primer.

12. The method of claim 11, wherein the forward nested primer is one selected from the group consisting of SEQ ID NO: 1, SEQ ID NO: 3, SEQ ID NO: 4 and SEQ ID NO: 10.

13. The method of claim 11, wherein the reverse nested primer is SEQ ID NO: 2 or SEQ ID NO: 9.

* * * * *

```
                         SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: EML4(E12)-Foward Primer Sequence

<400> SEQUENCE: 1
cacacctggg aaaggaccta                                              20

<210> SEQ ID NO 2
<211> LENGTH: 24
<212> TYPE: DNA
<213> ORGANISM: Artificial Sequence
<220> FEATURE:
<223> OTHER INFORMATION: ALK(E20)-Reverse Primer Sequence

<400> SEQUENCE: 2
actactgctt tgctggcaag acct                                         24

<210> SEQ ID NO 3
<211> LENGTH: 20
<212> TYPE: DNA
<213> ORGANISM: Artificial Sequence
<220> FEATURE:
<223> OTHER INFORMATION: EML4(E1E2)-Foward Primer Sequence

<400> SEQUENCE: 3
ccaaaactgc agacaagcat                                              20

<210> SEQ ID NO 4
<211> LENGTH: 24
<212> TYPE: DNA
<213> ORGANISM: Artificial Sequence
<220> FEATURE:
<223> OTHER INFORMATION: EML4(E4)-Foward Primer Sequence

<400> SEQUENCE: 4
cacaaattcg agcatcacct tctc                                         24

<210> SEQ ID NO 5
<211> LENGTH: 24
```

```
<212> TYPE: DNA
<213> ORGANISM: Artificial Sequence
<220> FEATURE:
<223> OTHER INFORMATION: Control Foward Primer Sequence

<400> SEQUENCE: 5
gtgcagtgtt tagcattctt gggg                                              24

<210> SEQ ID NO 6
<211> LENGTH: 24
<212> TYPE: DNA
<213> ORGANISM: Artificial Sequence
<220> FEATURE:
<223> OTHER INFORMATION: Control Reverse Primer Sequence

<400> SEQUENCE: 6
gtgcagtgtt tagcattctt gggg                                              24

<210> SEQ ID NO 7
<211> LENGTH: 22
<212> TYPE: DNA
<213> ORGANISM: Artificial Sequence
<220> FEATURE:
<223> OTHER INFORMATION: Control Forward Primer Sequence

<400> SEQUENCE: 7
gtcagctctt gagtcacgag tt                                                22

<210> SEQ ID NO 8
<211> LENGTH: 23
<212> TYPE: DNA
<213> ORGANISM: Artificial Sequence
<220> FEATURE:
<223> OTHER INFORMATION: Control Reverse Primer Sequence

<400> SEQUENCE: 8
atccagttcg tcctgttcag agc                                               23

<210> SEQ ID NO 9
<211> LENGTH: 23
<212> TYPE: DNA
<213> ORGANISM: Artificial Sequence
<220> FEATURE:
<223> OTHER INFORMATION: 3078RR Primer Sequence

<400> SEQUENCE: 9
atccagttcg tcctgttcag agc                                               23

<210> SEQ ID NO 10
<211> LENGTH: 24
<212> TYPE: DNA
<213> ORGANISM: Artificial Sequence
<220> FEATURE:
<223> OTHER INFORMATION: Fusion RT-S Primer Sequence

<400> SEQUENCE: 10
gtgcagtgtt tagcattctt gggg                                              24
```